United States Patent [19]

Rothkopf

[11] Patent Number: 5,179,080
[45] Date of Patent: Jan. 12, 1993

[54] FORMULATIONS CONTAINING GROWTH HORMONE AND NUTRITIONAL SUPPLEMENTS, AND METHODS OF TREATING MALNUTRITION IN CHRONIC LUNG DISEASE

[75] Inventor: Michael Rothkopf, North Caldwell, N.J.

[73] Assignee: Clinical Homecare, Corp., Fairfield, N.J.

[21] Appl. No.: 401,046

[22] Filed: Aug. 31, 1989

[51] Int. Cl.$^5$ .................. A61K 37/36; A61K 37/02
[52] U.S. Cl. .......................... 514/12; 514/2; 514/21; 514/561; 514/23; 514/547; 514/552; 514/560; 424/600
[58] Field of Search ............ 514/2, 12, 21, 549, 514/552, 560; 424/600

[56] References Cited

U.S. PATENT DOCUMENTS

| | | | |
|---|---|---|---|
| 3,697,287 | 10/1972 | Winitz | 424/74 |
| 3,698,912 | 10/1972 | Winitz | 514/561 |
| 3,793,450 | 2/1974 | Schell | 424/195 |
| 3,853,832 | 12/1974 | Li | 530/399 |
| 3,920,838 | 11/1975 | Flatt et al. | 424/319 |
| 3,950,529 | 4/1976 | Fischer et al. | 424/273 |
| 4,496,689 | 1/1985 | Mitra | 525/54.1 |
| 4,497,800 | 2/1985 | Larson et al. | 514/2 |
| 4,600,582 | 7/1986 | Stevens et al. | 514/2 |
| 4,600,583 | 7/1986 | Stevens et al. | 514/2 |
| 4,690,820 | 9/1987 | Simko | 424/128 |
| 4,699,897 | 10/1987 | Jones et al. | 514/4 |
| 4,775,659 | 10/1988 | Thakkar | 514/12 |
| 4,786,501 | 11/1988 | Janski | 424/422 |
| 4,791,099 | 12/1988 | Aroonsakul | 514/2 |
| 4,801,456 | 1/1989 | Drengler | 424/422 |
| 4,816,437 | 3/1989 | Nimberg et al. | 514/8 |
| 4,863,901 | 9/1989 | Wilmore | 514/12 |

OTHER PUBLICATIONS

Machlin, *Environmental Quality and Safety*, vol. 5 (Supplement) 43-53, 1976.
Chalupa et al., Symposium on Nutrient Partitioning, California Animal Nutrition Conference, Fresno, CA., 1987.
Suchner et al., *Anesthesiology*, 69, A421, 1988.
Vandenberg, E., et al., Am. Rev. Respir. Dis., 95:556-566 (1967), "Weight Changes in the Terminal Stages of Chronic Obstructive Pulmonary Disease".
Burrows, B., et al., Am. Rev. Respir. Dis., 91:665-678 (1963), "Chronic Obstructive Lung Disease".
Tiech, S. (incorrectly cited as Rogers), et al., Chest, 85:635-665 (1984), "Azygos Lymph Node Enlargement as Initial Manifestation of Underlying Disease".
Goldstein, S., et al., Chest, 91:222-224 (1987), "Energy Expenditure in Patients with Chronic Obstructive Pulmonary Disease".
Sukumalchantra, Y., et al., Am. J. Med., 39:941-945 (1965), "Serial Studies of Pulmonary Function in Patients with Chronic Obstructive Pulmonary Disease".
Goldstein, S., et al., Am. Rev. Respir. Dis., 138:636-644 (1988), "Nitrogen and Energy Relationships in Malnourished Patients with Emphysema".
Askanazi, J., et al., Surgery, 87:596-598 (1980), "Respiratory Distress Secondary to a High Carbohydrate Load: A Case Report".
Li, C., et al., Science, 124:1293-1294 (1956), "Preparation and Properties of Growth Hormone from Human and Monkey Pituitary Glands".
Li, C., et al., J. Amer. Chem. Soc., 88:2050-2051 (1966), "Human Pituitary Growth Hormone, XII, The Amino Acid Sequence of the Hormone".

(List continued on next page.)

Primary Examiner—F. T. Moezie
Attorney, Agent, or Firm—Bryan Cave

[57] ABSTRACT

Methods of treating malnutrition associated with chronic lung diseases comprising the administration of metabolically active peptides in an amount sufficient to increase circulating somatomedin C levels more than 0.8 U/ml plasma above the patient's baseline SmC level, along with nutritional supplementation providing a daily caloric intake of between 100% and 200% of the patient's baseline resting energy expenditure; and formulations utilized therein.

14 Claims, 1 Drawing Sheet

OTHER PUBLICATIONS

*Atlas of Protein Sequence and Structure,* vol. 5, Supp., 120–121 (1976).

Fryklund, L. M., et al., *Clinics in Endocrinology and Metabolism,* vol. 15, No. 3, 511–535 (1986), "Recombinant Human Growth Hormone".

Capdevielle, J., et al., Horm. Res., 24:225 (1986), "Characterization of Authentic Human Growth Hormone Produced in *Escherichia coli*".

Phares, C. K., J. Recept. Res., 8(5):645–665 (1988), "Use of Receptor Affinity Chromatography in Purification of the Growth Hormone–Like Factor Produced by Plerocercoids of the Tapeworm *Spirometra Mansonoides*".

*The Merck Index,* 10 ed., p. 1246, "Somatomedins".

D'Ercole, A. J. et al., Diabetes, 33:590–595 (1984), "Serum Somatomedin-C Concentrations in a Rabbit Model of Diabetic Pregnancy".

Harris et al., "A Biometric Study of the Basal Metabolism in Man", Carnegie Inst., Washington Pub., 279, pp. 223–250 (1919).

Elwyn, D. H., et al., Am. J. Clin. Nut., 32:1597–1611 (1979), "Changes in Nitrogen Balance of Depleted Patients With Increasing Infusions of Glucose".

Swift et al., *Energy Metabolism and Nutrition,* Scarecrow Press, Washington, DC (1954), pp. 3–4 and table of contents.

Gertz, I., et al., Clin. Sci. Mol. Med., 52:395–403 (1977), "Muscle Metabolism in Patients with Chronic Obstructive Lung Disease and Acute Respiratory Failure".

"Growth Hormone and Pulmonary Disease", Suchner, U., et al., Arch. Intern. Med., 150:1225–1230 (Jun. 1990).

Askanazi, J., Anesthesiology, 60(2):106–110 (1984), "Effect of Protein Intake on Ventilatory Drive".

Rochester, D. F., et al., Am. Rev. Respir. Dis., 119:151–154 (1979), "Respiratory Muscle Strength in Chronic Obstructive Pulmonary Disease".

Koruda, M. J., et al., IEEE Engineering in Medicine and Biology, 5:19–24 (1988).

Swift et al., Energy Metabolism and Nutrition, Scarecrow Press, Wash., DC, pp. 59–102 (1954).

Conzolazio et al., Physiological Measurements of Metabolic Function in Man, pp. 313–339 McGraw Hill, New York (1963).

FORMULATIONS CONTAINING GROWTH HORMONE AND NUTRITIONAL SUPPLEMENTS, AND METHODS OF TREATING MALNUTRITION IN CHRONIC LUNG DISEASE

TECHNICAL FIELD

This invention relates to formulations of metabolically active peptides and nutritional supplements, and to methods of treatment of malnutrition in chronic lung diseases therewith.

BACKGROUND OF THE INVENTION

The present invention is directed to formulations and methods of treating malnutrition associated with chronic lung diseases. Chronic lung diseases include diseases such as chronic obstructive pulmonary disease (COPD), cystic fibrosis and interstitial lung disease. A common characteristic of these diseases is the decreased capacity of lungs to exchange oxygen and carbon dioxide. This causes the patient to breathe faster which increases the energy the patient must expend in order to obtain enough oxygen.

Malnutrition is a common complication in these patients resulting from the increased energy needed to breathe as well as the reduced oral intake of food. This often results in weight loss which leads to a decline in pulmonary function. Severe weight loss is associated with a poor prognosis and increased mortality. Sukumalchantra, et al. *Am. J Med*, 39:941–945 (1965); Vandenbergh, et al., *Am Rev Respir Dis*, 95:556–566 (1967); Burrows, et al., *Am Rev Respir Dis*. 91:665–678 (1963); and Tiech, S., *Chest*. 85:635–665(1984).

Nutritional repletion regimens have been used in order to improve pulmonary function of patient's having chronic lung diseases. However, the physiologic response of individuals who suffer from these diseases pose significant challenges. This is particularly the case since the metabolism of certain nutrients, especially carbohydrates, used in these regimens results in both increased metabolic demands and ventilatory requirements due to excessive quantities of $CO_2$ produced from the metabolism of carbohydrates.

Goldstein, et al. *Chest*, 91:222–224 (1987) studied the energy expenditures of patients with COPD. Two hypercaloric formulations for use in refeeding patients with malnutrition were compared; a carbohydrate-based formulation consisting of a calorie distribution of 53% carbohydrate, 30% fat and 17% protein, and a fat-based formulation consisting of 55% fat, 28% carbohydrate and 17% protein. The patients were administered these two hypercaloric nutritional supplements in amounts equivalent to 1.7 times the amount of calories measured by the patients' resting energy expenditure (REE). Goldstein et al. concluded that diet-induced increases in energy expenditure occurred in patients with COPD and were accentuated by a moderately high carbohydrate diet.

In a later publication, *Am. Rev. Resp. Dis.*, 138, pp. 636–644 (1988), utilizing the same two hypercaloric formulations Goldstein et al. demonstrated that increased body weight, nitrogen balance and muscle strength were obtained by nutritional supplementation of 1.7 times the resting energy expenditure. This study also illustrated the problem of increased metabolic demand and ventilatory requirements associated with carbohydrate supplementation.

As the above studies show, the $CO_2$ produced from the metabolism of carbohydrate used for nutritional repletion decreased the patient's overall respiratory function and complicated ventilatory management. The decrease in respiratory function that occurred from these prior nutritional repletion regimens could be so severe that patients treated with aggressive hypercaloric nutritional regimens with high carbohydrate levels have been known to lapse into respiratory distress from the high levels of $CO_2$. Askanazi, et al. *Surgery*, 87:596–598 (1980) described a case of respiratory distress due to the high carbohydrate load of a total parenteral nutrition (TPN) formulation.

The foregoing studies demonstrate that patients with chronic lung diseases have altered metabolic states which require careful selection of the components used in nutritional formulations. Furthermore, traditional hypercaloric nutritional supplementation formulations, as demonstrated above, must be adjusted for the specialized needs of patients who suffer from chronic lung diseases. Thus, there exists a continuing need for nutritional formulations to treat chronic lung diseases and induce the beneficial effects associated therewith.

BRIEF DESCRIPTION OF THE DRAWING

The accompanying drawing is a graph showing the changes in fat, carbohydrate and protein oxidation and balance achieved during administration of human growth hormone and nutritional supplement exemplified in accordance with the present invention.

SUMMARY OF THE INVENTION

Figure 1A:
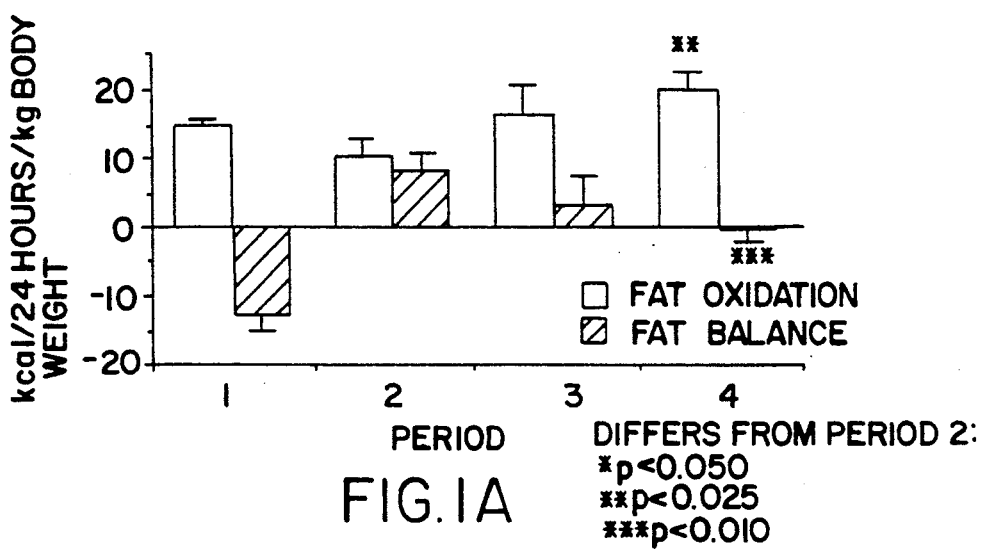

In accordance with the present invention, nutritional formulations and methods of treating malnutrition associated with chronic lung diseases are provided, which combine nutritional supplementation with the administration of metabolically active peptides in order to provide nutritional repletion while minimizing the increased metabolic demands associated with previously proposed hypercaloric nutritional regimens. In particular, it has been found that substantial improvement in the treatment of malnutrition in patients having chronic lung diseases is obtained by the concurrent administration of a metabolically active peptide in an amount sufficient to increase the circulating somatomedin C level to more than 0.8 U/ml above baseline SmC level before treatment, and a nutritional supplement in an amount providing a daily caloric intake in the range of from about 100 to 200% of the patient's baseline resting energy expenditure (REE), preferably from about 130 to 170% of the patient's baseline REE, the supplement providing less than about 300 grams of carbohydrates per day.

As used herein, the "treatment of malnutrition associated with chronic lung diseases" includes administration of the formulations described below to prevent the nutritional depletion known to occur in these diseases, as well as the treatment of malnutrition resulting from such diseases.

It has been found that the administration of a metabolically active peptide in conjunction with nutritional supplementation significantly increases the nitrogen balance, decreases the respiratory quotient and enhances fat oxidation while reducing carbohydrate oxidation in chronic lung disease patients. The combined therapy thus provides a technique for refeeding such patients without increasing metabolic demands and ventilatory requirements associated with the high carbohydrate loading of conventional hypercaloric nutritional supplementation.

As used herein, the term "metabolically active peptide" refers to those peptides which exhibit the metabolic effects associated with human pituitary growth hormone (hGH) and which are believed to be so active by reason of increasing somatomedin C levels in vivo by more than 0.8 U/ml above the baseline SmC level before treatment, preferably more than between 1.0 and 3.0 U/ml, more preferably between 1.4 and 2.5 U/ml. Metabolically active peptides having such effect comprise peptides or peptide analogs known to bind to human growth hormone releasing factor receptors, human growth hormone receptors or somatomedin-C receptors; human growth hormone; human growth hormone analogs; synthetic or naturally occurring peptides having primary structural homology to the amino acid residues of a particular region of human growth hormone; human growth hormone releasing factor (hGRF); human growth hormone releasing factor analogs; and the somatomedins per se, including somatomedin analogs and somatomedin C.

Human growth hormone (hGH) is a peptide whose isolation and structure is known (See Li et al., *Science,* 124, 1293 (1956); Li, et al., Journal of the American Chemical Society, 88, 2050 (1966); and Atlas of Protein Sequence and Structure, Vol. 5, Supp. 2 pp. 120-121 (1976). It has also been prepared by total syntheses as described, e.g., in Li U.S. Pat. No. 3,853,832, granted Dec. 10, 1974 and has also been prepared by recombinant DNA technology. (See "Recombinant Human Growth Hormone" L. M. Fryklund et al., *Clinics in Endocrinology and Metabolism* 15:3 (August 1986) and Capdevielle, J. et al. "Characterization of Authentic Human GH Produced in E. Coli" *Horm. Res.* 24:225 (1986))

hGH is a relatively high molecular weight polypeptide consisting of 188-191 amino acid residues and having a secondary structure provided by two disulfide bridges linking cysteine residues at particular positions in the molecule (see Li U.S. Pat. No. 3,853,832 at column 1, lines 21-30, and the somewhat different characterization in Jones et al U.S. Pat. No. 4,699,897, at column 2, lines 59-66.)

hGH is a potent anabolic hormone normally produced by the anterior pituitary gland, which produces a variety of metabolic effects. It affects the metabolic processes of the body by increasing the rate of cellular protein synthesis as well as the utilization of amino acids, and decreasing protein degradation along with the rate of use of carbohydrates for the production of energy in the body. Thus, hGH is known to increase nitrogen and protein balance, increase fat oxidation and decrease carbohydrate oxidation.

Human growth hormone analogs useful as metabolically active peptides in accordance with this invention include methionyl-hGH.

Metabolically active peptides which have primary structural homology to a particular region within hGH comprise those biologically active synthetic peptides disclosed in Jones et al. U.S. Pat. No. 4,699,897, granted Oct. 13, 1987, the disclosure of which is incorporated by their reference herein. Specifically, such peptides comprise those having primary structural homology to a continuous sequence of the amino acid residues of hGH in a region spanning positions 32 to 46, i.e., "hGH$_{32}$-46", NH$_2$-Glu-Glu-Ala-Tyr-Ile-Pro-Lys-Glu-Gln-Lys-Tyr-Ser-Phe-Leu-Gln-COOH.

Other peptides are known to exist or can be synthesized which bind to the same receptor as human growth hormone and would thus have the same effect as human growth hormone. For example, a growth hormone-like substance produced by the plerocercoid stage of the tapeworm Spirometra mansonoides is known to mimic the effects of human growth hormone. (See, Phases, CK "Use of receptor affinity chromatography in purification of the growth hormone like factor produced by pleroceroids of the tape worm Spirometra mansonoides." *J. Recept Res.* 8:645-665 (1988)).

Human Growth hormone-releasing Factor (hGRF) is a 44 amino acid peptide having growth hormone (hGH) releasing activity. As described in Drengler U.S. Pat. No. 4,801,456 granted Jan. 31, 1989, hGRF is usually isolated from pancreatic human tumor cells (hpGRF). hpGRF has the structure H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$.

Human growth hormone releasing factor analogs within the scope of the metabolically active peptides hereof comprise those analogs more fully described in the aforesaid Drengler U.S. Pat. No. 4,801,456, at column 1, line 22—column 2, line 34, the disclosure of which is incorporated by this reference herein. Other peptides are known or can be synthesized which bind to the same receptor as human growth hormone releasing factor and would have the same effect.

The somatomedins which may comprise the metabolically active peptides utilized in accordance with this invention are known in the literature, having been described in "Somatomedins" *The Merck Index,* 10 Ed. pg. 1246, the disclosure of which is incorporated by reference herein. The somatomedins are peptides having molecular weights of between 4500 and 7800 Daltons, which circulate in the body bound to larger carrier proteins. The somatomedins appear in the circulation within hours after hGH administration and have a half-life of about 12 hours. Somatomedin-C (SmC) is one of the somatomedins known to cause the same metabolic effects as hGH. Somatomedin-C, also known as IGF-1, is a basic, 70 amino acid single chain polypeptide with three disulfide bonds and a molecular weight of about 7700 Daltons.

Somatomedin-C exerts its effect by binding to specific receptors. Somatomedin-C analogs, which bind to these receptors, may be synthesized and can be used in place of Somatomedin-C. If such analogs were to be used, they would produce the same metabolic effect without increasing the levels of somatomedin levels.

Levels of Somatomedin-C are measured by radioimmunoassay techniques from commercially available kits utilizing methods disclosed in "Serum Somatoblatin-C Concentrations in a Rabbit Model of Diabetic Pregnancy by D'Encole, et al. *Diabetes* 33:590-595 (1984). Somatomedin levels are determined by obtaining samples of blood by venipuncture into tubes containing EDTA. Plasma is separated by centrifugation, placed into polypropylene tubes and rapidly cooled to 0° C.

It is currently believed that administration of the foregoing metabolically active peptides results in the synthesis or release in vivo of SmC, and that the metabolic effects attributable to hGH, hGRF or their respective analogs, result from the increase of the plasma level of SmC above about 1.90 U/ml, and preferably to above about 2.2 U/ml, more preferably between 2.5 and 3.5

U/ml plasma. Since plasma levels of SmC may vary with age, sex, nutritional status and other factors, it is preferable that a baseline level of SmC be established before the administration of metabolically active peptides. As used herein, the baseline level of SmC refers to the patient's untreated SmC plasma level. The resulting increase in SmC levels attributable to the metabolically active peptides is more than about 0.8 U/ml, preferably between about 1.0 and 3.0 U/ml, more preferably between about 1.4 to 2.5 U/ml above the baseline. It will, however, be understood that this invention is not restricted to the foregoing mechanism, but comprises the use of metabolically active peptides within the foregoing class which, as illustrated hereinafter, increase the nitrogen and protein balance, increase fat oxidation and decrease carbohydrate oxidation in patients having chronic lung diseases, whether by reason of the increase of SmC levels or otherwise.

The metabolically active peptide, preferably hGH, may be administered by any desired route, e.g., intranasally, sublingually, rectally, intramuscularly, intravenously or subcutaneously. For example, the metabolically active peptide can be administered parenterally in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

When the metabolically active peptide comprises recombinant DNA hGH, it is preferred to administer it subcutaneously, at a dosage of at least about 10-150 micrograms per kilogram of patient body weight per day, preferably between about 30 ug/kg/day to 60 ug/kg/day. Employing other metabolically active peptides, the specific dosage may vary depending upon the amount necessary to import the requisite metabolic activity in vivo.

As indicated hereinabove, the metabolically active peptide is concurrently administered, in accordance with this invention, with a nutritional supplement, the latter providing a daily caloric content in the range of from about 100 to 200%, preferably from about 130 to 170% of the patient's baseline resting energy expenditure (REE), and providing less than about 300 gm of carbohydrate per day. Baseline REE levels are the REE levels established before the administration of any nutritional supplementation.

The REE is a recognized parameter which may be predicted by application of the Harris-Benedict formula based upon the height, weight, age and sex of the patient. Harris, et al, "A Biometric Study of the Basal Metabolism in Man", Carnegie Inst. Washington Pub. 279, Washington, D.C. (1919). The REE may be calculated for an individual patient from his oxygen consumption ($VO_2$), carbon dioxide production ($VCO_2$) and nitrogen excretion by standard indirect calorimetry procedures. Elwyn, et al, American Journal of Clinical Nutrition, 32:1597-1611 (1979); Swift, et al, "Energy Metabolism and Nutrition", Scarecrow Press, Washington, D.C. (1954); and Consolazio, et al, "Physiological Measurements of Metabolic Function in Man", pages 313-339, McGraw Hill, N.Y. (1963).

Nutritional supplements useful in the treatment hereof comprise, by percentage of caloric intake, about 30 to 70% fat, 10 to 60% carbohydrate and 10 to 0% protein, preferably about 40 to 60% fat, 30 to 50% carbohydrates and 15 to 25% protein. They may also incorporate vitamins, electrolytes and mineral micronutrients. In order to minimize the increased metabolic demands produced by the administration of carbohydrate, the supplement has a minimum carbohydrate content, providing no more than about 300 grams per day.

Any commercially available protein source suitable for parenteral nutrition may be utilized in the nutritional supplement. Such protein source may comprise mixtures of essential and non-essential amino acids. For example, a formulation containing essential amino acids comprising isoleucine, leucine, lysine (acetate), methionine, phenylalanine, threonine, tryptophan and valine, and non-essential amino acids comprising alanine, arginine, aspartic acid, glutamic acid, histidine, proline, serine, N-acetyl-L-tyrosine and glycine (commercially available as "Aminosyn II" from Abbott Laboratories) may be utilized in the nutritional supplement.

The carbohydrate source incorporated in the nutritional supplement may be dextrose, glucose polymers, or starches. Preferably, the carbohydrate comprises dextrose administered in an amount of less than 300gm per day. A small proportion, from about 2 to 5 gms per day may be glycerol, incorporated in the fat emulsion utilized as a lipid source.

The fat source incorporated in the nutritional supplement may comprise triglycerides, lipids and/or free fatty acids. Preferably, the fat source may be a conventional fat emulsion incorporating an emulsifier such as a non-ionic surface active agent, egg yolk phospholipids and soybean phospholipids. Preferably, soybean oil is utilized as the fatty acid source.

Electrolytes and trace elements are readily available from various commercial sources. For example, TRACELYTE II WITH DOUBLE ELECTROLYTES containing sodium, potassium, calcium, magnesium, chloride, gluconate, acetate, zinc (as sulfate), copper (as sulfate), chromium (as chloride) and manganese (as sulfate), Potassium Phosphate Injection, U.S.P. and Magnesium Sulfate Injection, 50%, U.S.P., all from LyphoMed, Inc., Rosemont, IL, may be used. An additional example is ELIXIR FEOSOL containing iron from Smithkline Consumer Division, Philadelphia, Pa.

Vitamins in many forms are also suitable for use in the present invention. Examples include vitamin A, vitamin D, vitamin E, vitamin K, thiamine, riboflavin, pantothenic acid, niacin, pyridoxine, cyanocobalamin, ascorbic acid, biotin, folate and carnitine. These vitamins may be obtained from various commercial sources. For example, M.V.C. 9+3 from LyphoMed, Inc., Melrose Park, Ill. containing ascorbic acid, vitamin A as retinol, vitamin D as ergocalciferol, thiamine as the hydrochloride, riboflavin as the 5'-phosphate, pyridoxine as the hydrochloride, niacin as niacinamide, pantothenic acid as dexpanthenol, vitamin E as dl-alpha tocopheryl acetate, biotin, folate as folic acid and cyanocobalamin may be used. Additional examples include AQUA-MEPHYTOL INJECTION from Merck, Sharp and Dohme, West Point, Pa., containing vitamin K, and MEGA L-CARNITINE from Twin Labs, Ronkonkama, N.Y., containing carnitine.

The nutritional supplement may be administered either enterally or parenterally, and may provide the patient's entire nutritional requirements. Methods of administering enteral nutritional formulations are well known in the art and include oral, nasogastric tube or gastrostomy tube feeding techniques. Methods of providing parenteral nutritional supplementation are also well known in the art and include the use of peripheral catheters or central venous catheters.

Enteral supplementation can be provided by administration of the formulation made from the following components:

| Component | Quantity |
| --- | --- |
| Fish Oil Concentrate | 15–85 g |
| Wheat Germ Oil | 20–60 g |
| Carbohydrates | 215–315 g |
| Proteins | 102–124 g |
| Electrolytes | 8700–11500 mg |
| Trace Elements | 13–25 mg |
| Vitamins | 918–2470 mg |
| Emulsifiers | 5–50 g |
| Stabilizers | 0.2–3 g |
| Distilled Water | 1250–1295 ml |

Preferably, however, the nutritional supplement is administered by intravenous infusion. It has been shown that the infusion of intravenous lipids alters the patient's body fuel metabolism, thereby permitting caloric expenditure without the risk of a large increase in carbon dioxide production. This facilitates the use of parenteral nutrition in chronic lung disease patients because it permits the patients to receive large caloric quantities within tolerable limits of $CO_2$ production.

The co-administration of the aforesaid metabolically active peptide and nutritional supplement, either by the same route of administration, or by different routes, provides a pharmaceutical formulation having unique benefits in the treatment of patients suffering from malnutrition associated with chronic lung diseases. In particular, such benefits include producing a positive nitrogen balance, reduced utilization of carbohydrates, increased fat oxidation and accelerated restoration of lean body mass (LBM) along with decreased respiratory quotient (RQ). Surprisingly, these benefits are obtained by the use of nutritional supplementation which is less than the measured REE, i.e., is not hypercaloric.

DETAILED DESCRIPTION OF THE INVENTION

The following example illustrates a preferred embodiment of the present formulation and method for the treatment of malnutrition associated with chronic lung disease. It will be understood that the example is illustrative only, and does not limit the scope of this invention.

EXAMPLE

Six adult male patients with moderate to severe COPD and malnutrition were studied. Venous access was established using either a peripheral catheter (Aniocath, Deseret, Inc.) or a Hickman central venous catheter (Davol, Inc.)

On the first two days following the commencement of treatment (Period 1), the patients received D5W (dextrose and water) only.

On the next 4 days (period 2), the patients received total parenteral nutrition (TPN) with caloric intake adjusted to 130% of their baseline resting energy expenditure (REE) measured by indirect calorimetry. Baseline ree was determined on the date of admission. The TPN formulation consisted of 100 grams of fat (Intralipid 20%, Kabi-Vitrum, Inc.) 100 grams of carbohydrate (dextrose, 10%), 85 grams of protein (Travasol, Travenol Laboratories, Inc.), one ampule of vitamins (M.V.C. 9+3, Lyphomed, Inc.), and one ampule of trace elements (TMA, Abbott Laboratories, Inc.), administered in an amount calculated to 130 times the baseline REE per day. The caloric intake was distributed as follows: 59% fat, 20% carbohydrates and 21% protein; the calorie to nitrogen ratio (Kcal:gm) was about 119:1.

On the next four days (Period 3), TPN plus recombinant DNA biosynthetic human growth hormone were simultaneously administered subcutaneously, the hGH being administered at a rate of 30 ug/kg/day.

On the next 4 days (period 4), TPN plus recombinant DNA biosynthetic hGH were simultaneously administered, the hGH being administered at a dose of 60 ug/kg/day.

Balance Measurements

Intakes of each nutrient were calculated from differences in weights of full and used containers, and the composition specifications. 24 hour urine collections were analyzed for total nitrogen, urea and creatinine. Total nitrogen was determined by chemiluminescence using a Model 703C Analyzer (Antek Instruments, Inc., Houston, Tex.). Urea and creatinine were determined using a fast centrifugal analyzer (Instrumentation Laboratories, Lexington, Mass.).

Nitrogen balance was calculated from the difference between nitrogen intake and urinary excretion. In order to approximate the nitrogen content of stool and integumental losses a correction factor of 14.6 mg of nitrogen/kg body weight was added. The daily nitrogen balance was corrected for changes in plasma urea, assuming that urea was evenly distributed throughout body water. Total body water was estimated from regression equations relating to age, sex and weight. In order to estimate steady state conditions in each of the 4 day periods studied, the first two days were disregarded.

Somatomedin Concentration

Blood was collected in EDTA ("Lavender") tubes and plasma was separated by centrifugation. Plasma was placed in polypropylene tubes and rapidly cooled to 0° C. Somatomedin-C levels were measured by radioimmunoassay with commercially available kits (Somatomedin C-Nicholas Institute, San Juan Capistrano, Calif.).

Before the administration of growth hormone (periods 1 and 2), baseline somatomedin C (SmC) levels were between 0.91 U/ml and 1.04 U/ml. After the administration of growth hormone (periods 3 and 4), SmC levels rose to between 2.59 U/ml and 2.71 U/ml of plasma.

Nitrogen Balance

During D5W administration nitrogen balance was −7.6±2 (period 1). On TPN (period 2) it increased to near-zero (−0.25 ±3.6). Nitrogen balance did not increase significantly (0.26 ±3.7) with the addition of the low dose hGH in period 3. However, the addition of high dose hGH in period 4 resulted in a statistically significant increase in nitrogen balance (2±2.4) compared to TPN alone.

Fuel Oxidation and Fat Balance

Fat oxidation declined from 15±1 kcal/kg/day during period 1 to 11±2.4 in period 2. With the addition of hGH it rose to 16.3±4.4 kcal/kg/day in period 3 and 19/7±2.6 in period 4. Accordingly, fat balance decreased significantly from 8.5±2.3 kcal/kg/day in period 2 to −0.3±2 kcal/kg/day in period 4.

Carbohydrate oxidation was not changed between periods 1 and 2 (10.1±2.3 kcal/kg/day vs. 10±1.6 kcal/kg/day), but decreased significantly when hGH was added in period 3 (7.6±2 kcal/kg/day) and period 4 (5.2±1.6 kcal/kg/day). Compared to period 2, carbohydrate balance (−4.28±1.7) was significantly enhanced in periods 3 (−1.8±2.2) and 4 (0.7±2). The positive carbohydrate balance in period 4 indicates glycogen deposition.

There was no significant change in protein oxidation noted with the addition of hGH. Protein balance was positive throughout periods 2–4.

Energy Expenditure, Carbohydrate and Fat Oxidation

The addition of hGH to TPN elevated REE significantly. Since the caloric intake was established upon commencement of the study as equal to 130% of the baseline REE, the effect of growth hormone on energy requirements eventually brought the patients to near-zero energy balance. This is surprising in view of studies which showed that previous TPN formulations caused a significant positive energy balance to be maintained during TPN administration. The reduction in energy balance due to hGH would normally be expected to adversely effect nitrogen balance and muscle strength. However, the addition of hGH produced a surprising and beneficial increase in nitrogen balance in spite of the reduction in energy balance.

Nitrogen Metabolism

Corrected nitrogen balance increased significantly when hGH administration was added to TPN. With TPN alone it is expected that a steady state nitrogen balance will occur by day 4 of TPN.

The increase in nitrogen balance was much greater at the higher dose of hGH (period 4). However, in period 4, Somatomedin C levels did not change significantly relative to period 3. Thus, the continual increase in nitrogen balance represents an effect attributable to continuing exposure to hGH.

In view of the decrease in energy balance and stable nitrogen intake, the increase in nitrogen balance observed in period 4 is larger than would have been expected with TPN alone. This represents the strong hGH effect on nitrogen balance and suggests that hGH may lower the optimum Kcal/nitrogen ratio.

The nitrogen balance data is in accordance with the bioimpedance data which showed an increase in lean body mass during hGH administration. Calculations taken on the same day as the nitrogen balance and bioimpedance measurements showed a decrease in protein oxidation and an increase in protein balance.

Results

Oxygen utilization (VO2) increased and the respiratory quotient (RQ) declined when hGH was co-administered with TPN.

The accompanying figure demonstrates the beneficial metabolic changes produced when human growth hormone is administered in addition to TPN. The top graph compares fat oxidation and balance during each of the four periods in the study. During period 1 there is a negative fat balance and positive fat oxidation. When TPN is added (period 2) a positive fat balance is obtained. However, upon addition of human growth hormone to TPN in periods 3 and 4, fat oxidation increased and fat balance declined. This is beneficial since it indicates that more energy is being derived from the metabolism of fat.

The middle graph demonstrates that a positive carbohydrate balance is achieved through the addition of human growth hormone to TPN. During period 1, there is a negative carbohydrate balance. When TPN is administered (period 2) carbohydrate balance decreases further. However, upon administration of human growth hormone in addition to TPN, in period 3, carbohydrate balance is less negative when compared to TPN alone. A positive carbohydrate balance is achieved with continued administration of human growth hormone in period 4. This is beneficial since there is decreased carbohydrate oxidation which concommitant decreased production of $CO_2$.

The bottom graph demonstrates the increased nitrogen balance achieved though the administration of human growth hormone with TPN. During period 1, there is a negative nitrogen balance. Upon the administration of TPN, during period 2, a slight positive protein balance is seen. Upon administration of human growth hormone in periods 3 and 4, protein balance increases even further.

The data on substrate oxidation and balance show enhanced fat metabolism and reduced utilization of carbohydrates. Lipogenesis induced by TPN was progressively reduced when hGH was added, eventually changing to lipolysis and a loss of body fat stores upon continued administration of hGH. Carbohydrate oxidation decreased, producing glycogen storage by period 4. Protein oxidation decreased in accordance with the protein sparing effect of hGH. Somatomedin-C levels rose to levels about 1.6 U/ml above the baseline SmC levels.

These results show that treatment of patients with chronic lung disease by the simultaneous treatment of hGH and TPN stimulates nutritional repletion without increasing RQ.

When compared to patients treated with TPN alone, patients receiving hGH and TPN had less carbohydrate oxidation, more fat oxidation and a higher positive nitrogen balance.

It will be understood that various modifications may be made in the formulations and methods described above without departing from the scope of the present invention. Accordingly, the preceding disclosure should be construed as illustrative only and not in a limiting sense.

I claim:

1. A method for treating malnutrition in a patient having a chronic lung disease, comprising concurrently administering to a patient having a chronic lung disease, recombinant human growth hormone in an amount sufficient to increase circulating somatomedin C levels from 0.8 to 3.5 U/ml plasma above the patient's baseline plasma somatomedin C level, and total parenteral nutrition (TPN) comprising the following nutrients, in percentages of total caloric intake:

| Proteins | 10 to 30% |

| | |
|---|---|
| Carbohydrates | 10 to 60% |
| Fats | 30 to 70% | said TPN being administered in an amount providing a daily caloric intake in the range from 100 to 200% of the patient's resting energy expenditure.

2. The method of claim 1, wherein the daily caloric intake from the total parenteral nutrition is from 130 to 170% of the patient's resting energy expenditure.

3. The method of claim 1, wherein the recombinant human growth hormone is administered subcutaneously in an amount between 30 ug/kg/day and 50 ug/kg/day.

4. The method of claim 3, wherein the human growth hormone is administered in a time release formulation.

5. A method for treating malnutrition in a patient having a chronic lung disease, which comprises concurrently administering to the patient;
   a) human growth hormone in an amount sufficient to increase circulating somatomedin C levels from 0.8 to 3.5 U/ml plasma above the patient's baseline plasma somatomedin C level; and
   b) a nutritional supplement, in an amount providing a daily caloric intake in the range of from 100 to 200% of the patient's resting energy expenditure (REE), said supplement providing less than 300 g of carbohydrate per day.

6. The method of claim 5, wherein the daily caloric intake in said supplement is from 130 to 170% of the patient's baseline resting energy expenditure.

7. The method of claim 5, wherein the human growth hormone is recombinant human growth hormone, the human growth hormone is administered subcutaneously in an amount of between 30 ug/kg/day and 50 ug/kg/day, and the nutritional supplement is administered parenterally.

8. The method of claim 5, wherein the human growth hormone is administered in a time release formulation.

9. A nutrient formulation for a patient having a baseline circulating somatomedin level less than 1.0 U/ml plasma, which comprises in combination:
   (a) a human growth hormone in an amount which is sufficient to increase the patient's baseline circulating somatomedin C levels by from 1.0 to 3.5 U/ml plasma; and
   (b) a nutritional supplement in an amount providing a daily caloric intake from 100 to 200% of the patient's baseline resting energy expenditure, said nutritional supplement providing carbohydrates in an amount of 10 to 60% of total caloric content.

10. The formulation of claim 9, wherein the human growth hormone is recombinant human growth hormone in an amount of from 30 ug to 50 ug of the recombinant human growth hormone per kilogram of the patient's body weight per day.

11. The formulation of claim 9, wherein the human growth hormone is incorporated in a time release dosage.

12. The formulation of claim 9, wherein the nutritional formulation further comprises fats in an amount of 30 to 70% of total caloric content.

13. The formulation of claim 9, wherein the nutritional formulation further comprises proteins in an amount of 10 to 30% of total caloric content.

14. The formulation of claim 9, wherein the nutritional formulation further comprises vitamins, electrolytes, and mineral micronutrients.

* * * * *

UNITED STATES PATENT AND TRADEMARK OFFICE
CERTIFICATE OF CORRECTION

PATENT NO. : 5,179,080

DATED : January 12, 1993

INVENTOR(S): MICHAEL ROTHKOPF

Figure 1B:
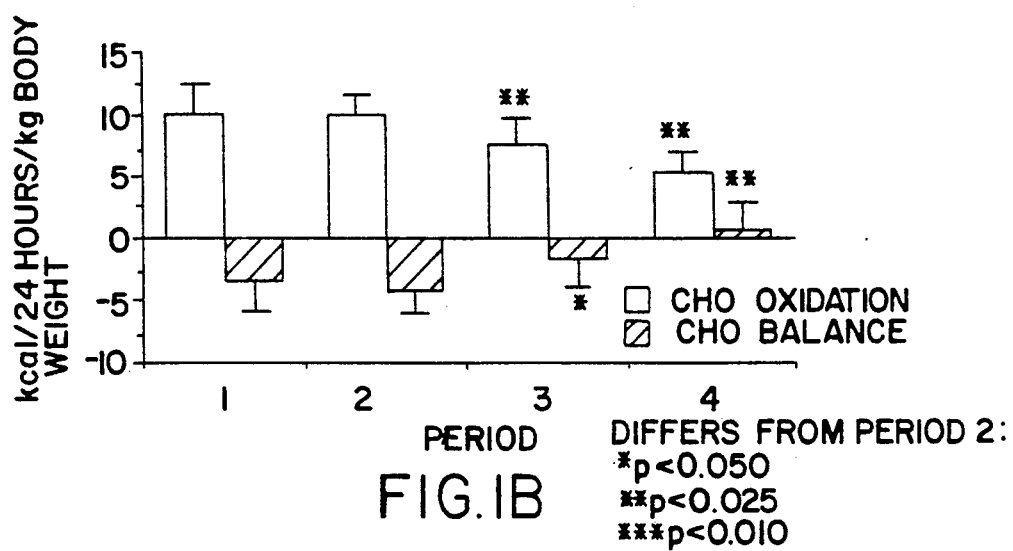
Figure 1C:
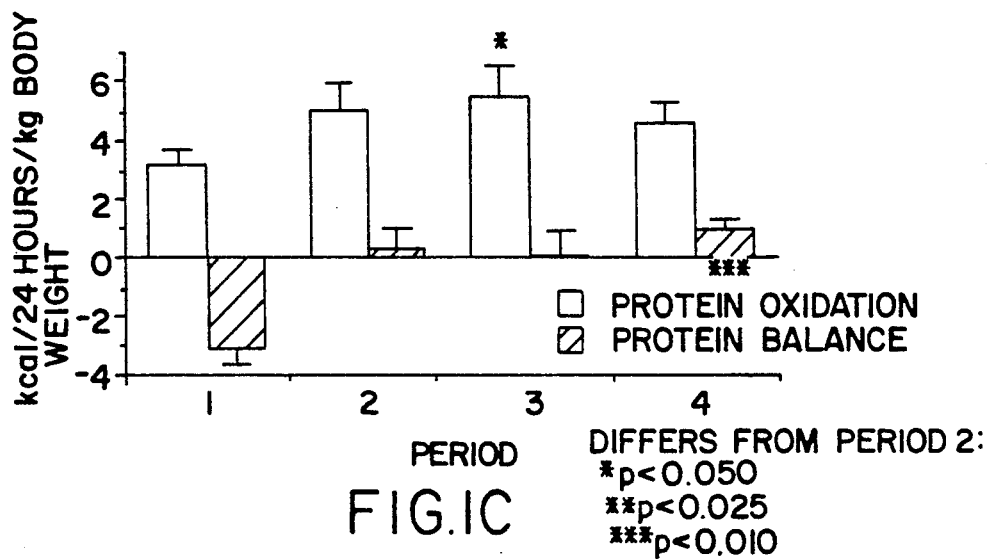

It is certified that error appears in the above-identified patent and that said Letters Patent is hereby corrected as shown below:

Column 2, line 26: Insert --(FIG. 1A-C)-- after "drawing". Same line delete "is a graph" and replace with --are graphs--.

Column 9, line 66: Insert --(FIG. 1A-C)-- after "figure".

Column 9, line 68: Insert --(FIG. 1A)-- after "top graph".

Column 10, line 10: Insert --(FIG. 1B)-- after "middle graph".

Column 10, line 23: Insert --(FIG. 1C)-- after "bottom graph".

Signed and Sealed this

Twenty-first Day of December, 1993

Attest:

BRUCE LEHMAN

*Attesting Officer*  *Commissioner of Patents and Trademarks*